(12) United States Patent
Spahn

(10) Patent No.: US 7,686,512 B2
(45) Date of Patent: Mar. 30, 2010

(54) X-RAY SYSTEM AND OPERATING METHOD FOR AN X-RAY SYSTEM

(75) Inventor: Martin Spahn, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 334 days.

(21) Appl. No.: 11/361,598

(22) Filed: Feb. 24, 2006

(65) Prior Publication Data

US 2006/0188063 A1   Aug. 24, 2006

(30) Foreign Application Priority Data

Feb. 24, 2005  (DE) .................. 10 2005 008 572

(51) Int. Cl.
*G01D 18/00* (2006.01)
*H05G 1/08* (2006.01)
*H05G 1/54* (2006.01)
*H05G 1/56* (2006.01)
*H05G 1/58* (2006.01)

(52) U.S. Cl. .................. 378/207; 378/91; 378/114; 378/117

(58) Field of Classification Search .............. 378/91, 378/95, 162, 165, 207, 114, 117
See application file for complete search history.

(56) References Cited

U.S. PATENT DOCUMENTS 6,457,861 B1 * 10/2002 Petrick et al. ............... 378/207
7,125,166 B2 * 10/2006 Eck et al. .................... 378/207

FOREIGN PATENT DOCUMENTS

DE       103 32 834 A1     2/2005

\* cited by examiner

*Primary Examiner*—Allen C. Ho

(57) ABSTRACT

X-ray system with an x-ray radiation source, a digital solid-state image detector with a calibration facility acquiring calibration data in order to ensure an optimum image quality, whereby the x-ray system has at least one sensor or interacts with a sensor which detects any person who may be present in the vicinity, whereby the acquisition of the calibration data is initiated when no person has been detected by the at least one sensor.

6 Claims, 1 Drawing Sheet

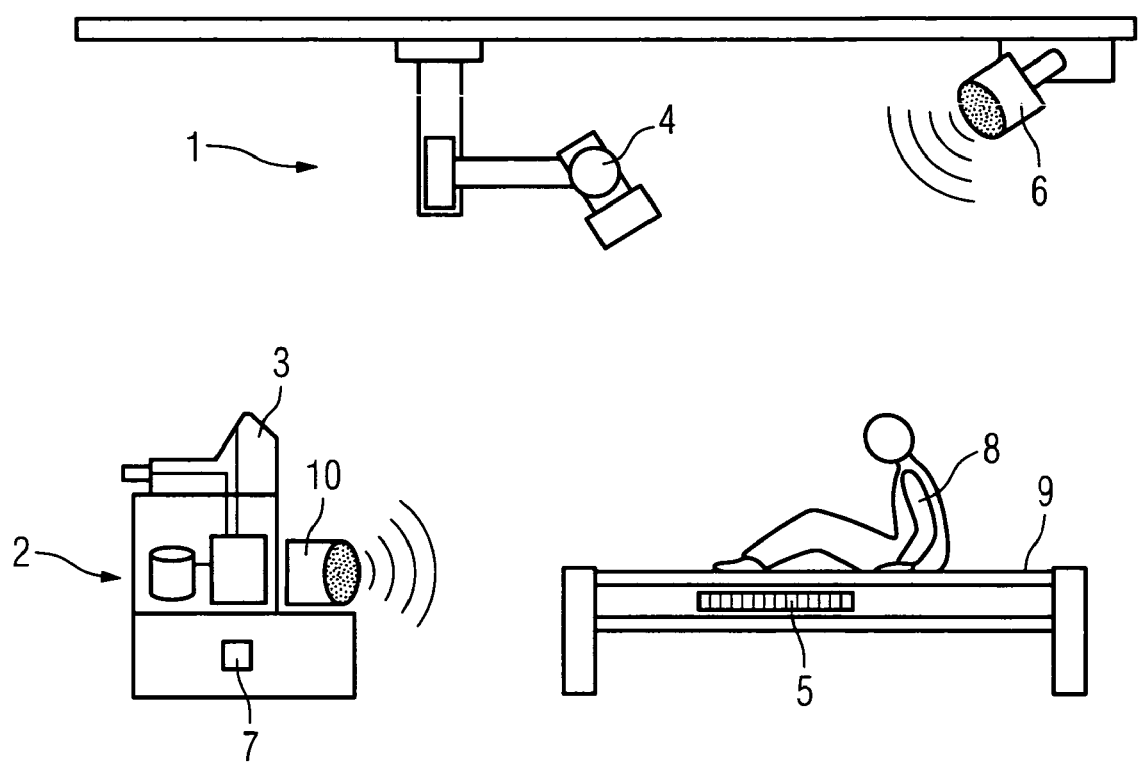

X-RAY SYSTEM AND OPERATING METHOD FOR AN X-RAY SYSTEM

CROSS REFERENCE TO RELATED APPLICATIONS

This application claims priority to the German Application No. 10 2005 008 572.5, filed Feb. 24, 2005 which is incorporated by reference herein in its entirety.

FIELD OF INVENTION

The invention relates to an x-ray system with an x-ray radiation source, a digital solid-state image detector with a calibration facility acquiring calibration data in order to ensure an optimum image quality.

BACKGROUND OF INVENTION

With regard to x-ray systems, a transition to digital imaging methods has been taking place for some time which has resulted in solid-state detectors being developed for digital x-ray imaging which are based on active readout matrices. The detectors are made of amorphous silicon (a-Si), the image information is converted in an x-ray converter, which is made of cesium iodide (CsI) for example, and converted into electrical charge and stored in photodiodes of the matrix. Similar technologies likewise use an active readout matrix made of amorphous silicon but employ a converter which generates electrical charge directly that is then stored on an electrode. The stored charge is subsequently read out by way of an active switching element with dedicated electronics and converted from analog to digital and processed further by an image system.

All semiconductor detectors, including digital solid-state images detectors in particular, require that the calibration data be regularly updated during operation. In order to achieve optimum quality of the x-ray images, so-called offset images are acquired without using x-ray radiation for the acquisition. After the exposure of the detector the image information is read out, followed by a reset phase. As a result of the acquisition of the calibration data in the form of offset images it is possible to compensate for interference effects which are caused by changes in temperature and other effects. Although a complete cycle for generating an offset image lasts only a few seconds, the acquisition of the calibration data by the x-ray system can only be initiated when the system is not active, in other words when no patient is present.

In practical applications the acquisition of the calibration data is normally performed automatically. With regard to conventional x-ray systems, an offset image is produced when no x-ray radiation has been applied during a predefined period of time. In this case it is assumed that there is no longer any patient in the examinant ion room and also that no x-ray radiation will be emitted in the immediate future which would prevent the acquisition of calibration data, for example as a result of the acquisition of offset images. This procedure results in relatively long time intervals being defined for the acquisition of the calibration data, with the result that the calibration data is not acquired in close temporal proximity. However, this solution is less than optimal in respect of the temperature dependency of detectors based on semiconductors but also in the case of detectors based on amorphous silicon.

DE 103 32 834 A1 describes a method for defect detection in the case of a digital x-ray detector and also an associated x-ray unit, in which are specified a method for the automatic detection of defective sensor elements of an x-ray detector and also an x-ray unit suitable for implementing the method. In this situation, an x-ray detector is provided which comprises a readout matrix applied to a substrate and which is provided with an illumination unit. The readout matrix is irradiated by means of the illumination unit with light of a predefined light intensity and a calibration image is acquired in the thus illuminated state. Using the calibration image, defective sensor elements are identified by means of a calibration unit, the number of defective sensor elements is ascertained and a warning message is issued when this number exceeds a predefined limit value.

SUMMARY OF INVENTION

An object of the invention is to specify an x-ray system in which the acquisition of calibration data is prevented when a patient or an operator is located in the vicinity of the x-ray system.

This object is achieved according to the invention in the case of an x-ray system of the type mentioned at the beginning by the fact that provision is made for the x-ray system to have at least one sensor or to interact with a sensor which detects any person who may be present in the vicinity, whereby acquisition of the calibration data is initiated if no person has been detected by the at least one sensor.

In a manner different to conventional x-ray systems, the acquisition of calibration data does not take place after the passage of a defined period of time during which no x-ray radiation has been emitted but a sensor signal containing information about a person possibly present is fed to the x-ray system. In the simplest case in this situation this information can be a digital signal, whereby the value 0 states that no person is present and whereby the value 1 indicates that a person, for example a patient or an operator, is present. With regard to the x-ray system according to the invention, the situation is avoided in which calibration data is simply acquired after defined time intervals, whereby relatively long periods of time have previously been selected. Instead, with the aid of the sensor provided according to the invention it is possible for active acquisition to take place depending on whether or not a person is present. If no person is present in the vicinity the acquisition of calibration data is initiated until such time as the sensor detects the presence of a person. With regard to this event-driven acquisition of calibration data, the method ensures that a calibration has always been performed a short time prior to when x-ray images are to be produced.

The x-ray system according to the invention can detect the presence of a person particularly well when the or a sensor takes the form of an optical sensor. Optical sensors are able to detect the movements of people. If a patient is located in the vicinity of the x-ray system, this person can be detected when he or she moves. The same holds true if a person enters the room in which the x-ray system is set up or approaches the x-ray system.

Alternatively or additionally, provision can be made whereby the or a sensor takes the form of an acoustic sensor which detects the noise generated by any person who may be present. With regard to other embodiments of the x-ray system according to the invention, provision can be made whereby the or a sensor takes the form of a heat sensor or infrared sensor. Such types of sensors allow the presence of a person to be detected in a particularly reliable manner.

In a further embodiment of the invention, provision can be made whereby the or a sensor in the x-ray system according to the invention detects whether a person is located on an examination table and/or in front of a wall unit. This sensor can for example take the form of an optical sensor which is situated in the area of the examination table and detects the presence of the person. In a similar manner, a sensor mounted in the area of a wall unit can detect a person standing in front of a wall unit.

The x-ray system according to the invention operates particularly reliably, and delivers x-ray images of optimum quality, if it is designed to acquire calibration data as offset images. In this case, the offset images can always be acquired in an automated manner whenever the sensor or sensors have detected no person in the vicinity of the x-ray system.

In addition, the invention relates to an operating method for an x-ray system, having an x-ray radiation source, a digital solid-state image detector and a calibration facility which acquires calibration data in order to ensure an optimum image quality.

With regard to the operating method according to the invention, provision is made whereby the x-ray system has at least one sensor or interacts with a sensor which detects any person who may be present, whereby acquisition of the calibration data is initiated if no person has been detected by the at least one sensor.

BRIEF DESCRIPTION OF THE DRAWING

Further advantages and details of the invention are explained on the basis of an embodiment with reference to the FIGURE.

The FIGURE is a schematic representation and shows an x-ray system according to the invention.

DETAILED DESCRIPTION OF INVENTION

The x-ray system 1 consists essentially of an image station 2 with a monitor 3, an x-ray source integrated in a ceiling support 4 for generating the x-rays and an image receiver system incorporating a detector 5. Operation and control of the x-ray system 1 are handled in a known manner by way of the image station 2 at which the requisite settings are undertaken by an operator. The components of the x-ray system 1, namely the image station 2, the ceiling stand 4 with the x-ray source and the detector 5 are connected to one another in a known manner by way of lines not shown in the FIGURE.

The detector 5 takes the form of a solid-state detector and is based on an active readout matrix made of amorphous silicon (a-Si). The image information received from the readout matrix is converted in an x-ray converter consisting of cesium iodide (CsI) and converted into electrical charge in photodiodes of the matrix and stored there. The stored charge is subsequently read out by way of a n active switching element with dedicated electronics and converted from analog to digital and processed further in the image station 2.

Since the detector 5 is a semiconductor detector, it is necessary to update calibration data at regular intervals. A calibration facility is provided for this purpose which is integrated in a control unit 7, by which means so-called offset images are continuously acquired by exposing the detector without x-ray radiation and subsequently reading out. In this way it is possible to compensate for influences which are caused by variations in temperature and other effects. As a result of the regular acquisition of these offset images it is possible to achieve an optimum image quality.

However, this calibration process, in other words the acquisition of offset images, can only be performed when no patient is located in the vicinity of the x-ray system 1. In order to avoid any undesired interruption of the work flow, the x-ray system 1 incorporates an optical sensor 6 which is mounted in the area of the x-ray source integrated in a ceiling support 4 on the ceiling of the examination room. The optical sensor 6 detects any persons who may be present in the area of its field of view, and sends a signal to the image station 2 which contains the control unit 7 with the calibration facility, through which the acquisition of the calibration data is initiated. When the optical sensor 6 has detected a person 8, who may be either a patient or an operator of the x-ray system 1, a corresponding signal is issued to the control unit 7. While a person 8 remains located in the vicinity of the x-ray system 1, in particular on the examination table 9, it is not possible to acquire an offset image. When the person 8 and all other persons possibly present have left the area of the x-ray system 1, this state is likewise detected by the optical sensor 6 and conveyed as a signal to the control unit 7 of the image station 2. The acquisition of calibration data can then be initiated by the control unit 7 such that the calibration facility is able to carry out a calibration.

An acoustic sensor 10 which reacts to noises generated by the person 8 is additionally mounted on the image station 2. The sensor 10 can be present in addition to the optical sensor 6, while in other embodiments simply the acoustic sensor 10 can be provided as the sole sensor. The acquisition of an offset image is prevented for as long as the acoustic sensor 10 detects a noise. If no noises have been detected during a defined period of time, it is possible to conclude from this that there are no persons currently located in the vicinity of the x-ray system 1, with the result that the acquisition of an offset image by the control unit 7 can be initiated. In this manner the method ensures that an acquisition of an offset image and a calibration of the solid-state detector 5 have taken place a short time prior to when x-ray images are to be produced by using the x-ray system 1.

The invention claimed is:

1. An X-ray system, comprising:
   an x-ray radiation source; and
   a digital solid-state image detector having a calibration facility for automated acquisition of calibration data to ensure an optimum image quality, wherein the X-ray system further comprises at least one presence sensor or is configured to communicate with a presence sensor via the calibration facility for detecting a person present in a vicinity of the X-ray system, wherein the calibration facility is effective to interrupt the acquisition of calibration data whenever a detecting result by the presence sensor indicates that there is a person present in the vicinity of the X-ray system and to automatically initiate acquisition of the calibration data when a detecting result by the presence sensor indicates that the person is no longer present in the vicinity of the X-ray system, and wherein the calibration data comprise offset images.

2. The X-ray system according to claim 1, wherein the presence sensor is an optical sensor.

3. The X-ray system according to claim 1, wherein the presence sensor is an acoustic sensor for detecting a noise generated by the person.

4. The X-ray system according to claim 1, wherein the presence sensor is a heat sensor or an infrared sensor.

5. The s-ray system according to claim 1, wherein the presence sensor is configured to detect if the person is located on an examination table or in front of a wall unit.

6. A method for operating an x-ray system having an x-ray radiation source, a digital solid-state image detector and a calibration facility for acquiring calibration data to ensure an optimum image quality, the method comprising:
   automatically determining if a person is present in a vicinity of the X-ray system by a presence sensor;

automatically initiating acquisition of calibration data upon determining no person is present in a vicinity of the X-ray system;

automatically interrupting the acquisition of calibration data whenever a detecting result by the presence sensor indicates that there is a person present in the vicinity of the X-ray system; and automatically initiating acquisition of calibration data when the presence sensor detects that the person is no longer present in the vicinity of the X-ray system, wherein the calibration data comprise offset images.

* * * * *